United States Patent
Barry et al.

(10) Patent No.: US 11,090,102 B2
(45) Date of Patent: *Aug. 17, 2021

(54) PREFERENTIAL VOLUME REDUCTION OF DISEASED SEGMENTS OF A HETEROGENEOUS LOBE

(71) Applicant: Uptake Medical Technology Inc., Seattle, WA (US)

(72) Inventors: Robert Lawrence Barry, Kirkland, WA (US); Erik Henne, Seattle, WA (US); Avina Gupta, Alta Loma, CA (US); Sourish Bandyopadhyay, Buena Park, CA (US)

(73) Assignee: Uptake Medical Technology Inc., Seattle, WA (US)

( * ) Notice: Subject to any disclaimer, the term of this patent is extended or adjusted under 35 U.S.C. 154(b) by 585 days.

This patent is subject to a terminal disclaimer.

(21) Appl. No.: 15/724,636

(22) Filed: Oct. 4, 2017

(65) Prior Publication Data

US 2018/0021078 A1   Jan. 25, 2018

Related U.S. Application Data

(63) Continuation of application No. 14/504,042, filed on Oct. 1, 2014, now Pat. No. 9,782,211.
(Continued)

(51) Int. Cl.
*A61B 18/04* (2006.01)
*A61B 34/10* (2016.01)
(Continued)

(52) U.S. Cl.
CPC .............. *A61B 18/04* (2013.01); *A61B 34/10* (2016.02); *A61B 5/08* (2013.01);
(Continued)

(58) Field of Classification Search
CPC combination set(s) only.
See application file for complete search history.

(56) References Cited

U.S. PATENT DOCUMENTS

| | | |
|---|---|---|
| 408,899 A | 8/1889 | Small |
| 1,719,750 A | 7/1929 | Bridge et al. |

(Continued)

FOREIGN PATENT DOCUMENTS

| | | |
|---|---|---|
| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Christian Jang
*Assistant Examiner* — Mitchell E Alter
(74) *Attorney, Agent, or Firm* — Richard Batt

(57) ABSTRACT

Methods and apparatus for diagnosing and treating disorders of the lung are provided, which may include any number of features. In one embodiment, a method comprises obtaining diagnostic information relating to a patient's lungs, compiling a list of potential treatment plans for lung volume reduction in the first and second lungs, excluding treatment plans from the list of potential treatment plans that propose treatment of a lung segment that falls within a segment exclusion rule, and identifying at least one preferred treatment plan from the list of potential treatment plans that targets sufficiently diseased lung segments while also targeting a preferred combined volume of the first and second lungs.

20 Claims, 10 Drawing Sheets

Related U.S. Application Data

(60) Provisional application No. 61/885,362, filed on Oct. 1, 2013.

(51) Int. Cl.
*A61B 18/00* (2006.01)
*A61B 5/08* (2006.01)

(52) U.S. Cl.
CPC ............ *A61B 2018/00285* (2013.01); *A61B 2018/00541* (2013.01); *A61B 2018/048* (2013.01); *A61B 2034/105* (2016.02)

(56) References Cited

U.S. PATENT DOCUMENTS

| | | | |
|---|---|---|---|
| 3,880,168 A | 4/1975 | Berman | |
| 4,026,285 A | 5/1977 | Jackson | |
| 4,773,410 A | 9/1988 | Blackmer et al. | |
| 4,793,352 A | 12/1988 | Eichenlaub | |
| 4,915,113 A | 4/1990 | Lolman | |
| 4,950,266 A | 8/1990 | Sinofsky | |
| 5,006,119 A | 4/1991 | Acker et al. | |
| 5,011,566 A | 4/1991 | Hoffman | |
| 5,084,043 A | 1/1992 | Hertzmann et al. | |
| 5,112,328 A | 5/1992 | Taboada et al. | |
| 5,158,536 A | 10/1992 | Michael et al. | |
| 5,263,951 A | 11/1993 | Spears et al. | |
| 5,331,947 A | 7/1994 | Shturman | |
| 5,334,190 A | 8/1994 | Seiler | |
| 5,348,551 A | 9/1994 | Spears et al. | |
| 5,352,512 A | 10/1994 | Hoffman | |
| 5,424,620 A | 6/1995 | Cheon et al. | |
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,549,628 A | 8/1996 | Cooper et al. | |
| 5,562,608 A | 10/1996 | Michael et al. | |
| 5,575,803 A | 11/1996 | Cooper et al. | |
| 5,591,157 A | 1/1997 | Hennings et al. | |
| 5,620,440 A | 4/1997 | Heckele et al. | |
| 5,695,507 A | 12/1997 | Auth et al. | |
| 5,735,811 A | 4/1998 | Brisken | |
| 5,752,965 A | 5/1998 | Francis et al. | |
| 5,755,753 A | 5/1998 | Knowlton | |
| 5,782,914 A | 7/1998 | Schankereli | |
| 5,800,482 A | 9/1998 | Pomeranz et al. | |
| 5,824,703 A | 10/1998 | Clark, Jr. | |
| 5,827,268 A | 10/1998 | Laufer | |
| 5,913,856 A | 6/1999 | Chia et al. | |
| 5,957,919 A | 9/1999 | Laufer | |
| 5,964,752 A | 10/1999 | Stone | |
| 5,972,026 A | 10/1999 | Laufer et al. | |
| 5,986,662 A | 11/1999 | Argiro et al. | |
| 5,989,445 A | 11/1999 | Wise et al. | |
| 6,032,077 A | 2/2000 | Pomeranz | |
| 6,053,909 A | 4/2000 | Shadduck | |
| 6,059,011 A | 5/2000 | Giolo | |
| 6,083,255 A | 7/2000 | Laufer et al. | |
| 6,099,251 A | 8/2000 | Lafleur | |
| 6,102,037 A | 8/2000 | Koch | |
| 6,113,722 A | 9/2000 | Hoffman et al. | |
| 6,130,671 A | 10/2000 | Argiro | |
| 6,131,570 A | 10/2000 | Schuster et al. | |
| 6,139,571 A | 10/2000 | Fuller et al. | |
| 6,156,036 A | 12/2000 | Sussman et al. | |
| 6,162,232 A | 12/2000 | Shadduck | |
| 6,179,805 B1 | 1/2001 | Sussman et al. | |
| 6,194,066 B1 | 2/2001 | Hoffman | |
| 6,200,333 B1 | 3/2001 | Laufer | |
| 6,210,404 B1 | 4/2001 | Shadduck | |
| 6,219,059 B1 | 4/2001 | Argiro | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,299,633 B1 | 10/2001 | Laufer | |
| 6,300,150 B1 | 10/2001 | Venkatasubramanian | |
| 6,312,474 B1 | 11/2001 | Francis et al. | |
| 6,327,505 B1 | 12/2001 | Medhkour et al. | |
| 6,394,949 B1 | 5/2002 | Crowley et al. | |
| 6,398,759 B1 | 6/2002 | Sussman et al. | |
| 6,398,775 B1 | 6/2002 | Perkins et al. | |
| 6,409,723 B1 | 6/2002 | Edwards | |
| 6,411,852 B1 | 6/2002 | Danek et al. | |
| 6,458,231 B1 | 10/2002 | Wapner et al. | |
| 6,468,313 B1 | 10/2002 | Claeson et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,575,929 B2 | 6/2003 | Sussman et al. | |
| 6,579,270 B2 | 6/2003 | Sussman et al. | |
| 6,585,639 B1 | 7/2003 | Kotmel et al. | |
| 6,588,613 B1 | 7/2003 | Pechenik et al. | |
| 6,589,201 B1 | 7/2003 | Sussman et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,629,951 B2 | 10/2003 | Laufer et al. | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,676,628 B2 | 1/2004 | Sussman et al. | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,719,738 B2 | 4/2004 | Mehier | |
| 6,755,794 B2 | 6/2004 | Soukup | |
| 6,770,070 B1 | 8/2004 | Balbierz | |
| 6,776,765 B2 | 8/2004 | Soukup et al. | |
| 6,860,847 B2 | 3/2005 | Alferness et al. | |
| 6,885,888 B2 | 4/2005 | Rezai | |
| 6,901,927 B2 | 6/2005 | Deem et al. | |
| 6,904,909 B2 | 6/2005 | Deem et al. | |
| 6,907,881 B2 | 6/2005 | Suki et al. | |
| 6,911,028 B2 | 6/2005 | Shadduck | |
| 6,986,769 B2 | 1/2006 | Nelson et al. | |
| 6,997,189 B2 | 2/2006 | Biggs et al. | |
| 7,022,088 B2 | 4/2006 | Keast et al. | |
| 7,027,869 B2 | 4/2006 | Danek et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester et al. | |
| 7,144,588 B2 | 12/2006 | Nicholas et al. | |
| 7,175,644 B2 | 2/2007 | Cooper et al. | |
| 7,192,400 B2 | 3/2007 | Campbell et al. | |
| 7,198,635 B2 | 4/2007 | Danaek et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| 7,412,977 B2 | 8/2008 | Fields et al. | |
| 7,422,563 B2 | 9/2008 | Roschak et al. | |
| 7,422,584 B2 | 9/2008 | Loomas et al. | |
| 7,425,212 B1 | 9/2008 | Danek et al. | |
| 7,462,162 B2 | 12/2008 | Phan et al. | |
| 7,628,789 B2 | 12/2009 | Soltesz et al. | |
| 7,708,712 B2 | 5/2010 | Phan et al. | |
| 7,740,017 B2 | 6/2010 | Danek et al. | |
| 7,778,704 B2 | 8/2010 | Rezai et al. | |
| 7,815,590 B2 | 10/2010 | Cooper | |
| 7,819,908 B2 | 10/2010 | Ingenito | |
| 7,906,124 B2 | 3/2011 | Laufer et al. | |
| 7,913,698 B2 | 3/2011 | Barry et al. | |
| 7,985,187 B2 | 7/2011 | Wibowo et al. | |
| 7,993,323 B2 | 8/2011 | Barry et al. | |
| 8,002,740 B2 | 8/2011 | Willink et al. | |
| 8,088,127 B2 | 1/2012 | Mayse et al. | |
| 8,172,827 B2 | 5/2012 | Deem et al. | |
| 8,187,269 B2 | 5/2012 | Shadduck et al. | |

(56) References Cited

U.S. PATENT DOCUMENTS

| | | |
|---|---|---|
| 8,251,070 B2 | 8/2012 | Danek et al. |
| 8,292,882 B2 | 10/2012 | Danek et al. |
| 8,322,335 B2 | 12/2012 | Barry et al. |
| 8,585,645 B2 | 11/2013 | Barry et al. |
| 8,734,380 B2 | 5/2014 | Barry et al. |
| 8,858,549 B2 | 10/2014 | Shadduck et al. |
| 8,900,223 B2 | 12/2014 | Shadduck |
| 2002/0077516 A1 | 6/2002 | Flanigan |
| 2002/0111386 A1 | 8/2002 | Michael et al. |
| 2002/0112723 A1 | 8/2002 | Schuster et al. |
| 2002/0177846 A1 | 11/2002 | Mulier et al. |
| 2003/0055331 A1* | 3/2003 | Kotmel ............. A61B 6/541 600/410 |
| 2003/0099279 A1 | 5/2003 | Venkatasubramanian et al. |
| 2003/0181922 A1 | 9/2003 | Alferness |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0055606 A1 | 3/2004 | Hendricksen et al. |
| 2004/0068306 A1 | 4/2004 | Shadduck |
| 2004/0199226 A1 | 10/2004 | Shadduck |
| 2004/0200484 A1 | 10/2004 | Springmeyer |
| 2004/0244803 A1 | 12/2004 | Tanaka |
| 2005/0016530 A1 | 1/2005 | Mccutcheon et al. |
| 2005/0066974 A1 | 3/2005 | Fields et al. |
| 2005/0166925 A1 | 8/2005 | Wilson et al. |
| 2005/0171396 A1 | 8/2005 | Pankratov et al. |
| 2005/0171582 A1 | 8/2005 | Matlock |
| 2005/0203483 A1 | 9/2005 | Perkins et al. |
| 2005/0215991 A1 | 9/2005 | Altman et al. |
| 2005/0222485 A1 | 10/2005 | Shaw et al. |
| 2006/0004400 A1 | 1/2006 | Mcgurk et al. |
| 2006/0047291 A1 | 3/2006 | Barry |
| 2006/0100619 A1 | 5/2006 | Mcclurken et al. |
| 2006/0130830 A1 | 6/2006 | Barry |
| 2006/0135955 A1 | 6/2006 | Shadduck |
| 2006/0162731 A1 | 7/2006 | Wondka et al. |
| 2006/0200076 A1 | 9/2006 | Gonzalez et al. |
| 2006/0224154 A1 | 10/2006 | Shadduck et al. |
| 2007/0032785 A1 | 2/2007 | Diederich et al. |
| 2007/0036417 A1 | 2/2007 | Argiro et al. |
| 2007/0068530 A1 | 3/2007 | Pacey |
| 2007/0091087 A1 | 4/2007 | Zuiderveld |
| 2007/0092864 A1 | 4/2007 | Reinhardt et al. |
| 2007/0102011 A1 | 5/2007 | Danek et al. |
| 2007/0106292 A1 | 5/2007 | Kaplan et al. |
| 2007/0109299 A1 | 5/2007 | Peterson |
| 2007/0112349 A1 | 5/2007 | Danek et al. |
| 2007/0118184 A1 | 5/2007 | Danek et al. |
| 2007/0137646 A1 | 6/2007 | Weinstein et al. |
| 2007/0293853 A1 | 12/2007 | Truckai et al. |
| 2008/0033493 A1 | 2/2008 | Deckman et al. |
| 2008/0132826 A1 | 6/2008 | Shadduck et al. |
| 2009/0018538 A1 | 1/2009 | Webster et al. |
| 2009/0043301 A1 | 2/2009 | Jarrard et al. |
| 2009/0138001 A1 | 5/2009 | Barry et al. |
| 2009/0149846 A1 | 6/2009 | Hoey et al. |
| 2009/0192508 A1 | 7/2009 | Laufer et al. |
| 2009/0216220 A1 | 8/2009 | Hoey et al. |
| 2009/0301483 A1 | 12/2009 | Barry et al. |
| 2009/0312753 A1 | 12/2009 | Shadduck |
| 2010/0094270 A1 | 4/2010 | Sharma |
| 2010/0204688 A1 | 8/2010 | Hoey et al. |
| 2010/0256714 A1 | 10/2010 | Springmeyer |
| 2010/0262133 A1 | 10/2010 | Hoey et al. |
| 2010/0305463 A1 | 12/2010 | MacKlem et al. |
| 2011/0077628 A1 | 3/2011 | Hoey et al. |
| 2011/0160648 A1 | 6/2011 | Hoey |
| 2011/0172654 A1 | 7/2011 | Barry et al. |
| 2011/0257644 A1 | 10/2011 | Barry et al. |
| 2011/0270031 A1 | 11/2011 | Frazier et al. |
| 2011/0301587 A1 | 12/2011 | Deem et al. |
| 2012/0016363 A1 | 1/2012 | Mayse et al. |
| 2012/0016364 A1 | 1/2012 | Mayse et al. |
| 2013/0006231 A1 | 1/2013 | Sharma et al. |
| 2013/0267939 A1 | 10/2013 | Barry et al. |
| 2014/0275952 A1* | 9/2014 | Monroe ............. G06T 19/00 600/407 |
| 2015/0230852 A1 | 8/2015 | Barry et al. |

FOREIGN PATENT DOCUMENTS

| | | |
|---|---|---|
| EP | 1143864 B1 | 2/2004 |
| EP | 1173103 B1 | 10/2005 |
| EP | 1326549 B1 | 12/2005 |
| EP | 1326548 B1 | 1/2006 |
| EP | 1485033 B1 | 8/2009 |
| WO | 3011927 A2 | 3/2000 |
| WO | 3102042 A1 | 1/2001 |
| WO | 32069821 A1 | 9/2002 |
| WO | 33070302 A1 | 8/2003 |
| WO | 33086498 A2 | 10/2003 |
| WO | 2005025635 A2 | 3/2005 |
| WO | 2005102175 A2 | 11/2005 |
| WO | 2006003665 A2 | 1/2006 |
| WO | 2006052940 A2 | 5/2006 |
| WO | 2006053308 A2 | 5/2006 |
| WO | 2006053309 A2 | 5/2006 |
| WO | 2006080015 A2 | 8/2006 |
| WO | 2006116198 A2 | 11/2006 |
| WO | 2008051706 A2 | 5/2008 |
| WO | 2009009236 A1 | 1/2009 |
| WO | 2009009398 A1 | 1/2009 |
| WO | 2009015278 A1 | 1/2009 |
| WO | 2009137819 A1 | 11/2009 |
| WO | 2010042461 A1 | 4/2010 |
| WO | 2011056684 A2 | 5/2011 |
| WO | 2011060200 A1 | 5/2011 |
| WO | 2011060201 A1 | 5/2011 |
| WO | 2011127216 A2 | 10/2011 |

OTHER PUBLICATIONS

Blacker, G. F.; Vaporization of the uterus; J. of Obstetrics and Gynaecology; vol. 33; pp. 488-511; 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Clinical trials.gov.; Study of the AeriSeal System for Hyperinflation Reduction in Emphysema; 4 pages; Nov. 5, 2014 retrieved from the internet (http://clinicaltrials.gov/show/NCT01449292).

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

Delaunois; Anatomy and physiology of collateral respiratory pathways; Eur. Respir. J.; 2(9); pp. 893-904; Oct. 1989.

Eyal et al.; The acute effect of pulmonary burns on lung mechanics and gas exchange in the rabbit; Br. J. Anaesth. vol. 47; pp. 546-552; (year of publication is sufficiently earlier than the effective U.S. filing date and any foreign priority date) 1975.

Ferlay et al.; GLOBOCAN 2008 v1.2, Cancer Incidence and Mortality Worldwide: IARC CancerBase No. 10 [internet] 16 pages; retrieved from the Internet (http://www.iarc.fr/en/media-centre/iarcnews/2010/GLOBOCAN2008.pdf); Lyon, France: International Agency for Research on Cancer; Jun. 1, 2010.

Fishman et al., A randomized trial comparing lung-volume reduction surgery with medical therapy for severe emphysema, N Engl J Med, vol. 348, No. 21, pp. 2059-2073, May 22, 2003.

Goldberg et al.; Radiofrequency tissue ablation in the rabbit lung: Efficacy and complications; Acad. Radiol.; vol. 2; pp. 776-784; Sep. 1995.

Henne et al.; U.S. Appl. No. 14/957,433 entitled "Vapor treatment of lung nodules and tumors," filed Dec. 2, 2015.

Herth et al.; Efficacy predictors of lung volume reduction with zephyr valves in a european cohort; Eur. Respir. J.; 39 (6); pp. 1334-1342; Jun. 2012.

Homasson, et al., "Bronchoscopic cryotherapy for airway strictures caused by tumors," Chest, vol. 90, No. 2, pp. 159-164, Aug. 1986.

(56) References Cited

OTHER PUBLICATIONS

Kang, Li, "Efficient optimal net surface detection for image segmentation—from theory to practice," M.Sc. Thesis, The University of Iowa, Dec. 2003.
Kinsella et al.; Quantitation of emphysema by computed tomography using a "densitymask" program and correlation with pulmonary function tests; Chest; 97(2); pp. 315-321; Feb. 1990.
Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.
Marasso, et al., "Cryosurgery in bronchoscopic treatment of tracheobronchial stenosis," Chest, vol. 103, No. 2, pp. 472-474, Feb. 1993.
Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.
Mathur et al., Fiberoptic bronchoscopic cryotherapy in the management of tracheobronchial obstruction, Chest, vol. 110, No. 3, pp. 718-723, Sep. 1996.
Morice et al.; Endobrinchial argon plasma coagulation for treatment of hemotysis and neoplastic airway obstruction, Chest, vol. 119, No. 3, pp. 781-787, Mar. 2001.
Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.
Moulding et al.; Preliminary studies for achieving transcervical oviduct occlusion by hot water or low-pressure steam Advances in Planned Parenthood; vol. 12, No. 2; pp. 79-85; (year of publication is sufficiently earlier than the effective U.S. filing date and any foreign priority date) 1977.
National Lung Screening Trial Research Team; Reduced lung-cancer mortality with low-dose computed tomographic screening; N. Eng. J. Med.; 365(5); pp. 395-409; Aug. 4, 2011.
Pieter et al.; U.S. Appl. No. 15/013,748 entitled "Medical vapor generator," filed Feb. 2, 2016.
Pracht, Adam, "VIDA takes new approach," Iowa City Press-Citizen, Sep. 12, 2005.
Quin, Jacquelyn, "Use of neodymium yttrium aluminum garnet laser in long-term palliation of airway obstruction," Connecticut Medicine, vol. 59, No. 7, pp. 407-412, Jul. 1995.
Sciurba et al.; A randomized study of endobronchial valves for advanced emphysema; N. Eng. J. Med.; 363(13); pp. 1233-1244; Sep. 23, 2010.
Shah et al.; Collateral ventilation and selection of techniques for bronchoscopic lung volume reduction; Thorax; 67(4) pp. 285-286; Apr. 2012.
Slebos et al.; Bronchoscopic lung volume reduction coil treatment of patients with severe heterogeneous emphysema Chest; 142(3); pp. 574-582; Sep. 2012.
Sutedja, et al.; Bronchoscopic treatment of lung tumors; Elsevier, Lung Cancer, 11, pp. 1-17, Jul. 1994.
Tschirren et al.; Intrathoracic airway trees: segmentation and airway morphology analysis from low-dose CT scans IEEE Trans. Med. Imaging; vol. 24, No. 12; pp. 1529-1539; Dec. 2005.
Tschirren, Juerg; Segmentation, anatomical labeling, branchpoint matching, and quantitative analysis of human airway trees in volumetric CT images; Ph.D. Thesis; The University of Iowa; Aug. 2003.
Tschirren, Juerg; Segmentation, anatomical labeling, branchpoint matching, and quantitative analysis of human airway trees in volumetric CT images; Slides from Ph.D. defense; The University of Iowa; Jul. 10, 2003.
Van De Velde; Vapo-cauterization of the uterus; Amer. J. Med. Sci.; vol. CXVIII; (year of publication is sufficiently earlier than the effective U.S. filing date and any foreign priority date) 1899.
Vorre et al.; Morphology of tracheal scar after resection with C02-laser and high-frequency cutting loop; Acta Dtolaryngol (Stockh); vol. 107; pp. 307-312; (year of publication is sufficiently earlier than the effective U.S. filing date and any foreign priority date) 1989.

* cited by examiner

| U00000001M | LUL | LB1 | LB2 | LB3 | LB1+2 | RUL | RB1 | RB2 | RB3 |
|---|---|---|---|---|---|---|---|---|---|
| Method 1 | | 2 | 3 | | | | 1 | | |
| Method 2 | | 2 | | 3 | | | 1 | | |
| Method 3 | | | 2 | 3 | | | 1 | | |
| Method 4 | | | | | 2 | | 1 | | |
| Method 5 | | 2 | 3 | | | | | 1 | |
| Method 6 | | 2 | | 3 | | | | 1 | |
| Method 7 | | | 2 | 3 | | | | 1 | |
| Method 8 | | | | | 2 | | | 1 | |
| Method 9 | | 2 | 3 | | | | | | 1 |
| Method 10 | | 2 | | 3 | | | | | 1 |
| Method 11 | | | 2 | 3 | | | | | 1 |
| Method 12 | | | | | 2 | | | | 1 |
| Method 13 | | | | | 1 | | 2 | 3 | |
| Method 14 | | | | | 1 | | 2 | | 3 |
| Method 15 | | | | | 1 | | | 2 | 3 |
| Method 16 | | | | 1 | | | 2 | 3 | |
| Method 17 | | | | 1 | | | 2 | | 3 |
| Method 18 | | | | 1 | | | | 2 | 3 |
| Method 19 | | | 1 | | | | 2 | 3 | |
| Method 20 | | | 1 | | | | 2 | | 3 |
| Method 21 | | | 1 | | | | | 2 | 3 |
| Method 22 | | 1 | | | | | 2 | 3 | |
| Method 23 | | 1 | | | | | 2 | | 3 |
| Method 24 | | 1 | | | | | | 2 | 3 |
| Method 25 | | 1 | | | | | 2 | | |
| Method 26 | | | 1 | | | | 2 | | |
| Method 27 | | | | 1 | | | 2 | | |
| Method 28 | | 2 | | | | | | 1 | |
| Method 29 | | | 2 | | | | | 1 | |
| Method 30 | | | | 1 | | | | 2 | |
| Method 31 | | 1 | | | | | | | 2 |
| Method 32 | | | 1 | | | | | | 2 |
| Method 33 | | | | 1 | | | | | 2 |

FIG. 6A

|  |  | LB1 | LB2 | LB3 | LB1+2 |  | RB1 | RB2 | RB3 |
|---|---|---|---|---|---|---|---|---|---|
| TAR |  | 7.11% | 7.78% | 9.28% | 7.43% |  | 7.62% | 10.13% | 11.38% |
| HI | 2.389 | 2.65 | 2.42 | 2.03 | 2.53 | 2.40 | 2.95 | 2.22 | 1.98 |
| Air volume | 1206 | 478 | 437 | 291 | 915 | 1639 | 761 | 385 | 492 |
| Mass | 95 | 34 | 34 | 27 | 68 | 154 | 58 | 39 | 56 |
| Total Vol [M+V] | 1301 | 512 | 471 | 318 | 983 | 1793 | 819 | 424 | 548 |
| Per. of lobe [M+V] |  | 39% | 36% | 24% | 76% |  | 46% | 24% | 31% |
| LL TAR | 18.82% | ⇩ LLL TAR |  |  |  | 22.51% | ⇩ RLL TAR |  |  |

FIG. 6B

| U00000001M | Tx. 1 Size [30%-70%] | Tx. 1 Size [>1700ml] | Tx. 2 Size [40%-80%] | Tx. 2 Size [>1700ml] | Total Tx. Size [95%-130%] | Segmental HI and Mass |
|---|---|---|---|---|---|---|
| Method 1 | | | | | | |
| Method 2 | | | | | | |
| Method 3 | | | | | | |
| Method 4 | | | | | | LB1+2>=48g. |
| Method 5 | Tx. 1<30% | | | | | |
| Method 6 | Tx. 1<30% | | | | Tot Tx. <95% | |
| Method 7 | Tx. 1<30% | | | | Tot Tx. <95% | |
| Method 8 | Tx. 1<30% | | | | | LB1+2>=48g. |
| Method 9 | | | | | | |
| Method 10 | | | | | Tot Tx. <95% | |
| Method 11 | | | | | Tot Tx. <95% | |
| Method 12 | | | | | | LB1+2>=48g. |
| Method 13 | Tx. 1>70% | | | | Tot Tx. >130% | LB1+2>48g. |
| Method 14 | Tx. 1>70% | | | | Tot Tx. >130% | LB1+2>48g. |
| Method 15 | Tx. 1>70% | | | | | LB1+2>48g. |
| Method 16 | Tx. 1<30% | | | | Tot Tx. <95% | |
| Method 17 | Tx. 1<30% | | | | | |
| Method 18 | Tx. 1<30% | | | | Tot Tx. <95% | |
| Method 19 | | | | | | |
| Method 20 | | | | | | |
| Method 21 | | | | | Tot Tx. <95% | |
| Method 22 | | | | | | |
| Method 23 | | | | | | |
| Method 24 | | | | | Tot Tx. <95% | |
| Method 25 | | | | | Tot Tx. <95% | |
| Method 26 | | | | | Tot Tx. <95% | |
| Method 27 | Tx. 1<30% | | | | Tot Tx. <95% | |
| Method 28 | Tx. 1<30% | | Tx. 2<40% | | Tot Tx. <95% | |
| Method 29 | Tx. 1<30% | | Tx. 2<40% | | Tot Tx. <95% | |
| Method 30 | Tx. 1<30% | | Tx. 2<40% | | Tot Tx. <95% | |
| Method 31 | | | Tx. 2<40% | | Tot Tx. <95% | |
| Method 32 | | | Tx. 2<40% | | Tot Tx. <95% | |
| Method 33 | Tx. 1<30% | | Tx. 2<40% | | Tot Tx. <95% | |

FIG. 6C

| U00000001M | TAR-Seg 1 | TAR-Seg 2 | TAR-Seg 3 | Combined TAR | Total Tx [%] | % from Target [110%] |
|---|---|---|---|---|---|---|
| Method 1 | 7.62% | 7.11% | 7.78% | 7.52% | 121.2% | 11.23% |
| Method 2 | 7.62% | 7.11% | 9.28% | 7.78% | 109.5% | 0.53% |
| Method 3 | 7.62% | 7.78% | 9.28% | 7.99% | 106.3% | 3.68% |
| Method 4 | 7.62% | 7.43% | | 7.52% | 121.2% | 11.23% |
| Method 5 | 10.13% | 7.11% | 7.78% | 8.23% | 99.2% | 10.80% |
| Method 6 | 10.13% | 7.11% | 9.28% | 8.67% | 87.4% | 22.56% |
| Method 7 | 10.13% | 7.78% | 9.28% | 8.98% | 84.3% | 25.71% |
| Method 8 | 10.13% | 7.43% | | 8.23% | 99.2% | 10.80% |
| Method 9 | 11.38% | 7.11% | 7.78% | 8.81% | 106.1% | 3.88% |
| Method 10 | 11.38% | 7.11% | 9.28% | 9.28% | 94.4% | 15.64% |
| Method 11 | 11.38% | 7.78% | 9.28% | 9.59% | 91.2% | 18.79% |
| Method 12 | 11.38% | 7.43% | | 8.81% | 106.1% | 3.88% |
| Method 13 | 7.43% | 7.62% | 10.13% | 8.01% | 144.9% | 34.88% |
| Method 14 | 7.43% | 7.62% | 11.38% | 8.39% | 151.8% | 41.80% |
| Method 15 | 7.43% | 10.13% | 11.38% | 9.10% | 129.8% | 19.77% |
| Method 16 | 9.28% | 7.62% | 10.13% | 8.63% | 93.8% | 16.23% |
| Method 17 | 9.28% | 7.62% | 11.38% | 9.13% | 100.7% | 9.32% |
| Method 18 | 9.28% | 10.13% | 11.38% | 10.45% | 78.7% | 31.35% |
| Method 19 | 7.78% | 7.62% | 10.13% | 8.28% | 105.5% | 4.47% |
| Method 20 | 7.78% | 7.62% | 11.38% | 8.76% | 112.4% | 2.44% |
| Method 21 | 7.78% | 10.13% | 11.38% | 9.82% | 90.4% | 19.59% |
| Method 22 | 7.11% | 7.62% | 10.13% | 8.07% | 108.7% | 1.32% |
| Method 23 | 7.11% | 7.62% | 11.38% | 8.55% | 115.6% | 5.60% |
| Method 24 | 7.11% | 10.13% | 11.38% | 9.52% | 93.6% | 16.43% |
| Method 25 | 7.11% | 7.62% | | 7.43% | 85.0% | 24.97% |
| Method 26 | 7.78% | 7.62% | | 7.68% | 81.9% | 28.12% |
| Method 27 | 9.28% | 7.62% | | 8.08% | 70.1% | 39.88% |
| Method 28 | 10.13% | 7.11% | | 8.46% | 63.0% | 47.00% |
| Method 29 | 10.13% | 7.78% | | 8.88% | 59.9% | 50.15% |
| Method 30 | 9.28% | 10.13% | | 9.76% | 48.1% | 61.91% |
| Method 31 | 7.11% | 11.38% | | 9.28% | 69.9% | 40.08% |
| Method 32 | 7.78% | 11.38% | | 9.69% | 66.8% | 43.23% |
| Method 33 | 9.28% | 11.38% | | 10.60% | 55.0% | 54.99% |

FIG. 6D

PREFERENTIAL VOLUME REDUCTION OF DISEASED SEGMENTS OF A HETEROGENEOUS LOBE

CROSS REFERENCE TO RELATED APPLICATIONS

The present application is a Continuation of U.S. patent application Ser. No. 14/504,042, filed Oct. 1, 2014, which claims the benefit of U.S. Provisional Patent Application No. 61/885,362, filed Oct. 1, 2013, which is incorporated by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates generally to treatment of emphysema in the lung. The disclosure more specifically relates to vapor ablation of diseased lung tissue to treat emphysema.

BACKGROUND

Patients with severe emphysema typically have lung segments within a lobe that are significantly more diseased than other segments within that lobe. These more diseased segments of a lobe typically are more hyperinflated, and have the poorest function (gas exchange).

Reducing hyperinflation by reducing lung volume in patients with emphysema has been shown to improve pulmonary function and quality of life. Many current techniques to achieve LVR focus on an entire lung lobe without regard to variance in disease state among the segments of the lobe. For example, valves implanted in the lung rely on blockage of ventilation and subsequent atelectasis of an entire lobe to create LVR. Valves must occlude all segments of a lobe in order to achieve safe and effective LVR. This is because collateral ventilation occurs between segments within a lobe, and therefore all segments must be blocked in order for that lobe to have ventilation effectively blocked in its current embodiment.

Coils implanted in the lung rely on tissue retraction to create LVR. Coils are typically placed in up to 10 segments of each lung (upper and lower lobes). The therapy is reported to improve elastic recoil by whole lung reduction. A treatment regimen for coils targeting the most diseased segments is problematic as tissue retraction does not work as well in the most highly diseased segments due to lack of tissue to grab. Additionally, a large number of segments must be retracted with coils, making targeting less feasible.

Glue/foam therapy relies on blocking non-adjacent sub-segments with glue. Therefore if a two adjacent segments are both highly diseased one of those highly diseased sub-segments will not be reduced. Additionally, glue is delivered at the sub-segmental level due to limitations with patient tolerance of inflammatory reaction to glue.

SUMMARY OF THE DISCLOSURE

Many lung lobes contain segments that are not significantly hyperinflated. This invention provides a method to achieve pulmonary and quality of life improvement by treating only the highly diseased segments of a lobe. A method of treatment planning for lung volume reduction is provided, comprising obtaining diagnostic information relating to a patient's lungs, compiling a list of potential treatment plans for lung volume reduction in the first and second lungs, excluding treatment plans from the list of potential treatment plans that propose treatment of a lung segment that falls within a segment exclusion rule, and identifying at least one preferred treatment plan from the list of potential treatment plans that targets sufficiently diseased lung segments while also targeting a preferred combined volume of the first and second lungs.

In some embodiments, the diagnostic information comprises a tissue-to-air ratio, a heterogeneity index, an air volume, a mass, or a percentage of a lobe of each segment of the first and second lungs.

In one embodiment, compiling a list comprises compiling a list of potential treatments that include a first treatment that targets a first segment of a first lobe of the first lung, and a second treatment that targets a second segment of a second lobe of the second lung.

In one embodiment, the second treatment also targets a third segment of the second lobe of the second lung.

In some embodiments, the segment exclusion rule requires that treatment plans including segments that have a heterogeneity index under 1.2 be excluded.

In one embodiment, the segment exclusion rule requires that treatment plans including segments that have a mass less than 13 g be excluded.

In some embodiments, the segment exclusion rule requires that treatment plans including segments having a tissue mass in grams plus air volume in milliliters greater than 1700 be excluded.

In one embodiment, the segment exclusion rule requires that treatment plans including segments that have a mass greater than 48 g be excluded.

In some embodiments, the segment exclusion rule requires that treatment plans including treatment of the first lung that treats less than 30% of the first lung or more than 70% of the first lung be excluded.

In one embodiment, the segment exclusion rule requires that treatment plans including treatment of the second lung that treats less than 40% of the second lobe or more than 80% of the second lobe be excluded.

In one embodiment, the segment exclusion rule requires that treatment plans including a treatment of the first and second lungs resulting in less than 95% or greater than 130% of a combined percentage of the first and second lungs be excluded.

In alternative embodiments, the at least one preferred treatment plan requires treatment of segments with an insignificant difference in tissue-to-air ratios (TARs).

In other embodiments, the insignificant difference comprises a difference of less than 2% between the TARs of the proposed segments.

In some embodiments, the at least one preferred treatment plan requires treatment of segments that rank closes to 110% volume treated between a combined percentage of the first and second lungs to be treated.

In some embodiments, the at least one preferred treatment plan comprises applying lung volume reduction therapy to at least one lung segment in the first lung and at least one lung segment in the second lung.

In one embodiment, the lung volume reduction therapy comprises delivering condensable vapor to the patient's lungs.

A method of causing lung volume reduction in lungs of a patient is provided, comprising calculating a tissue-to-air ratio (TAR) of a plurality of lung segments in the lungs of the patient, comparing the TARs of the lung segments to identify healthy lung segments and diseased lung segments, and ablating only the diseased lung segments to cause lung volume reduction in the lungs of the patient in the presence of collateral ventilation.

In one embodiment, the ablating step comprises delivering vapor to the diseased lung segments.

A method of treatment planning for lung volume reduction in first and second lungs of a patient is provided, comprising calculating a tissue-to-air ratio of a plurality of lung segments in the first and second lungs, compiling a list of potential treatment plans for lung volume reduction in the first and second lungs, wherein each potential treatment plan includes treating a first segment in the first lung and a second segment in the second lung, excluding treatment plans from the list of potential treatment plans if the first or second lung segment has a heterogeneity index less than a threshold heterogeneity value, excluding treatment plans from the list of potential treatment plans if the first or second lung segment has a mass less than a minimum threshold mass, excluding treatment plans from the list of potential treatment plans if the first or second lung segment has a tissue mass plus an air volume greater than a threshold tissue mass plus air volume, excluding treatment plans from the list of potential treatment plans if the first or second lung segment has a mass greater than a maximum threshold mass, excluding treatment plans from the list of potential treatment plans if a volume percentage of the first or second lung segment falls outside a threshold range of a total volume of a first lobe or a second lobe, excluding treatment plans from the list of potential treatment plans if treatment of the first and second lung segments would result in a total treated tissue mass plus air volume greater than the threshold tissue mass plus air volume, and excluding treatment plans from the list of potential treatment plans if a combined volume percentage of the first and second lung segments falls outside a threshold range of a total volume of the first and second lungs.

In one embodiment, the threshold heterogeneity value is 1.2.

In another embodiment, the minimum threshold mass is 13 g.

In some embodiments, the threshold tissue mass in grams plus air volume in milliliters is 1700.

In one embodiment, the maximum threshold mass is 48 g.

In some embodiments, the threshold range of the total volume of the lobe comprises 30-70% of the total volume of the lobe.

In one embodiment, the threshold range of the total volume of the lobe comprises 40-80% of the total volume of the lobe.

In some embodiments, the threshold range of the total volume of the first and second lungs comprises 95%-130%.

In one embodiment, the method further comprises determining if a significant difference in tissue-to-air ratio exists between the first and second segments of each remaining treatment plan.

In some embodiments, the significant difference in tissue-to-air ratio is defined as a greater than 2% difference between the first and second segments.

In one embodiment, the method further comprises excluding treatment plans from the list of potential treatment plans that include the significant difference in tissue-to-air ratio between the first and second segments.

In one embodiment, the method further comprises, if a significant difference in tissue-to-air ratio between the first and second segments does not exist, calculating a combined tissue-to-air ratio for each treatment plan remaining from the list of potential treatment plans, and selecting treatment plans from the list of potential treatment plans that have a combined tissue-to-air ratio within a combined tissue-to-air ratio range.

In some embodiments, the combined tissue-to-air ratio range is 0.3%.

In one embodiment, the method further comprises ranking any remaining treatment plans from the list of potential treatment plans based on treating the total volume of the first and second lungs closest to an ideal total volume to be treated.

In one embodiment, the ideal total volume to be treated is approximately 110%.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-6D illustrate one example of treatment planning.

DETAILED DESCRIPTION

Vapor ablation of lung tissue can be used to treat lung disorders, such as emphysematous tissue. Application of vapor to emphysematous tissue can damage the tissue to create LVR. Compared to the techniques described above, the ablation of microvasculature with vapor results in elimination of diseased tissue supplied by that microvasculature. Since vapor travels along the airway tree and into the parenchyma, the vapor can shrink and cause fibrosis of the lung tissue, which can result in volume reduction in the presence of collateral ventilation. Vapor can be delivered preferentially to the most diseased segments within a lobe. Tissue-to-air ratio (TAR) can be used as a surrogate marker for extent of hyperinflation and degree of gas exchange deficiency. TAR can be derived from a HRCT scan.

Figure 1:
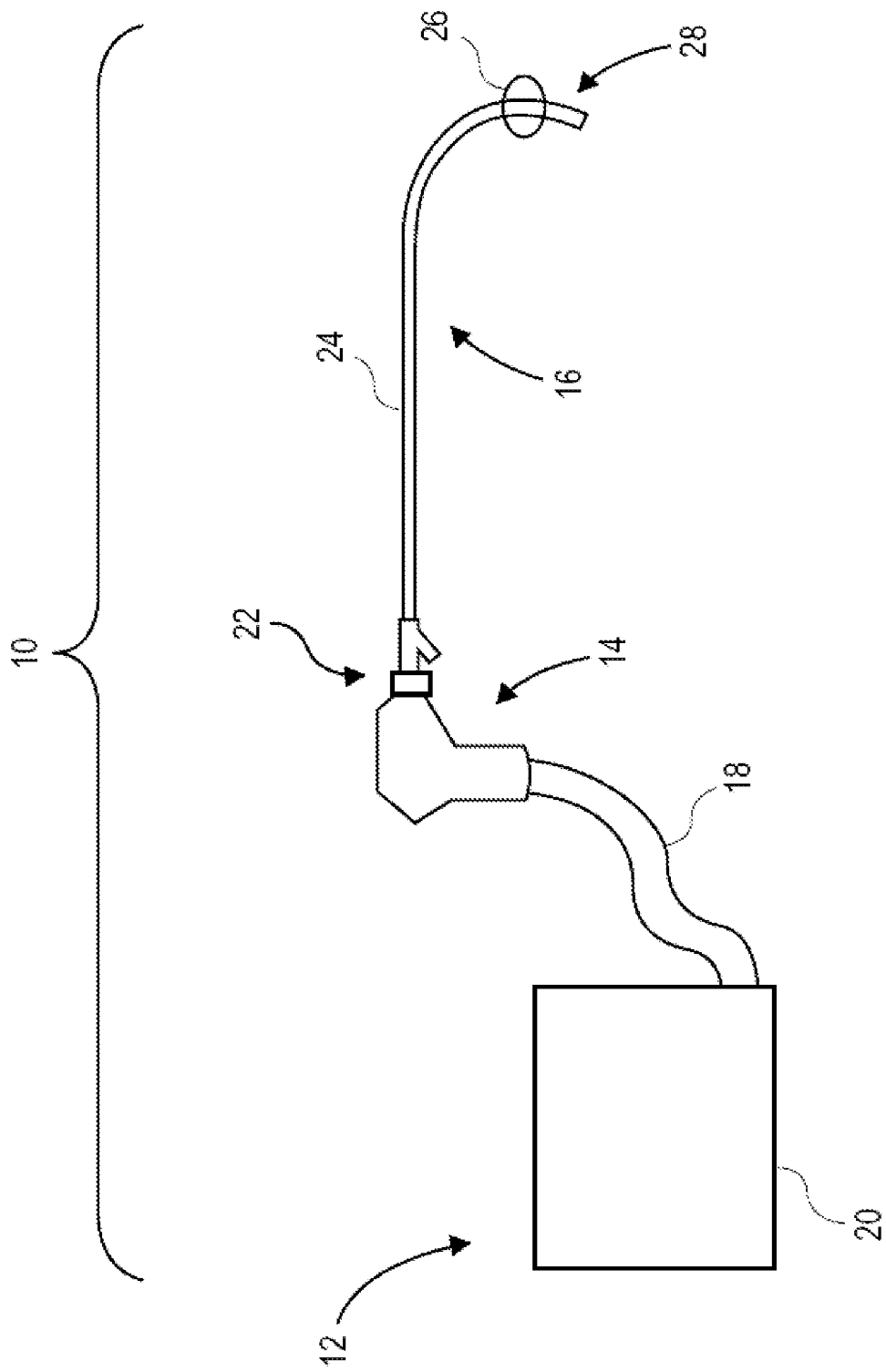
FIGS. 1-2 illustrate an embodiment of a vapor delivery system for lung volume reduction.
Figure 2:
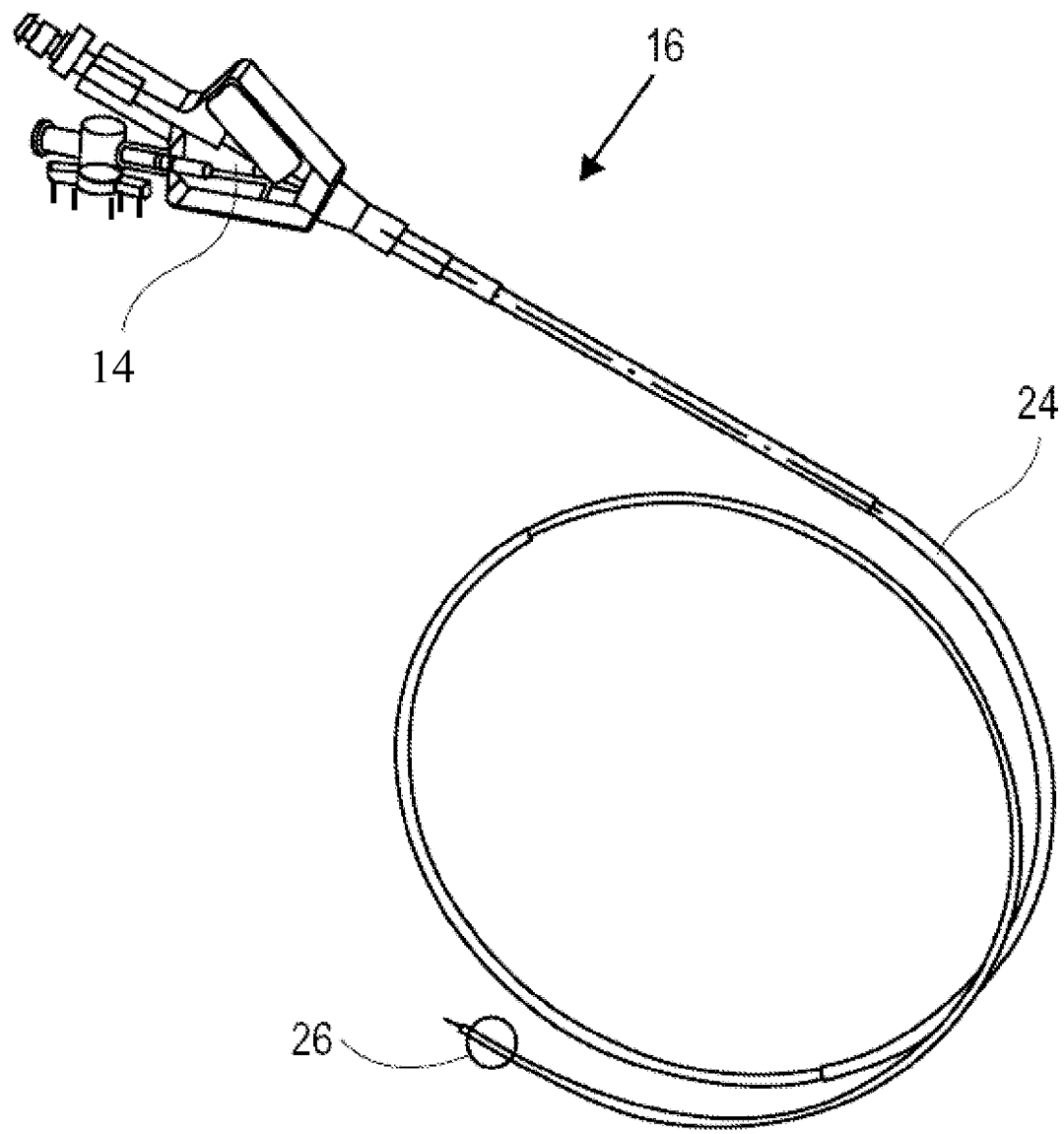

FIGS. 1-2 show one embodiment of a system 10 and system components for generating and delivering vapor to lung tissue to be treated. The system 10 generally comprises a vapor generator 12, hand-piece 14, and delivery catheter 16.

The vapor generator 12 can be attached to hand-piece 14 by tube 18. The generator can comprise a pressure vessel 20 containing liquid water (or other biocompatible liquid, such as saline) and a heating element (not shown) configured to heat the water or other biocompatible liquid to generate condensable vapor. In some embodiments, the vapor generator can further comprise sensors, such as temperature sensors, pressure sensors, and/or flow rate sensors, and valves to control the flow of vapor. Hand piece 14 can be coupled to the proximal end 22 of catheter 16. The vapor generator can further include a processor or electronic controller operatively connected to the vapor generator, the delivery catheter, and to sensors in the catheter and/or in the body of the patient, and the processor or electronic controller can be configured to control all aspects of vapor delivery from the generator through the catheter to a target tissue. Vapor generation and delivery can be controlled by the processor or controller based on a number of factors, including parameters of the system, of the vapor, or of the body of the patient sensed by the sensors or alternatively, based on an input from a user such as flow rate, dosage, or total volume of vapor to be delivered.

The catheter is generally used to deliver the heated condensable vapor (e.g., steam) to a targeted segment or sub-segment of the subject's lung containing the diseased lung tissue. The catheter 16 generally comprises flexible shaft 24 and occlusion balloon 26 located at or slightly proximal to the distal end 28 of the catheter. The distal end 28 of the catheter can include vapor ports for delivering the vapor to the targeted tissues. When the occlusion balloon 26 is expanded within a targeted segment or sub-segment of the lung, the delivered vapor is allowed to propagate distally into the lung, but not proximally past the occlusion balloon.

In some embodiments, the catheter can be introduced to a lung segment via the airway using a bronchoscope. Once a target airway with the diseased lung tissue is reached, vapor can be delivered from the catheter to ablate the lung tissue using the airway as a delivery channel or the open parenchymal space. This can be done with and without the occlusion balloon shown in FIGS. 1-2.

One limitation of the bronchoscope method is the diameter of the scope, since a bronchoscope cannot access airways smaller in diameter than the outer diameter of the bronchoscope. One method of delivering a more precise treatment is to access a more distal (and smaller) airway. To do this, a pulmonary navigation system could be used. There are a number of ways to implement this.

In one embodiment, system 10 of FIGS. 1-2 can further include a navigation catheter with a working channel. First, the navigation catheter can be navigated to the target airway using its navigation system. After the target airway is reached, the vapor catheter 16 can be pushed through the working channel to the target airway and to deliver vapor to ablate the tissue.

Another method is to incorporate the navigation system described above into the vapor catheter 16 of system 10. In this embodiment, the vapor catheter 16 is navigatable to the target tissue, without the need for a separate navigation catheter or bronchoscope to access the target site of the lungs. In this embodiment, the catheter is navigated to the target and then vapor is delivered to ablate the lung tissue.

The vapor is generally heated to between about 100° C. to about 200° C. in the vapor generator. Vapor generated in a remote boiler will typically have a lower temperature upon delivery, but the vapor will still have a temperature at or above at least 100° C.

Referring again to FIGS. 1-2, the vapor catheter is preferably non-reusable and supplied sterile. The catheter can comprise components for occluding the target airway and delivering a dose of vapor from the vapor generator to the targeted lung segment or sub-segment. The catheter shaft can be adapted to allow delivery of the catheter through a bronchoscope, and the catheter comprises a balloon near the distal end of the catheter shaft to allow proper sealing of the targeted bronchi.

A general method of delivering vapor to the lung includes advancing the catheter into the region of the lung targeted for treatment, such as a segment or sub-segment of the lung. The balloon 26 at or near the distal end of the catheter tip can be inflated to seal the airway. The vapor can then delivered from the distal end of the catheter to the targeted tissue. After treatment, the balloon can then deflated to allow for withdrawal of the catheter.

Figure 3:
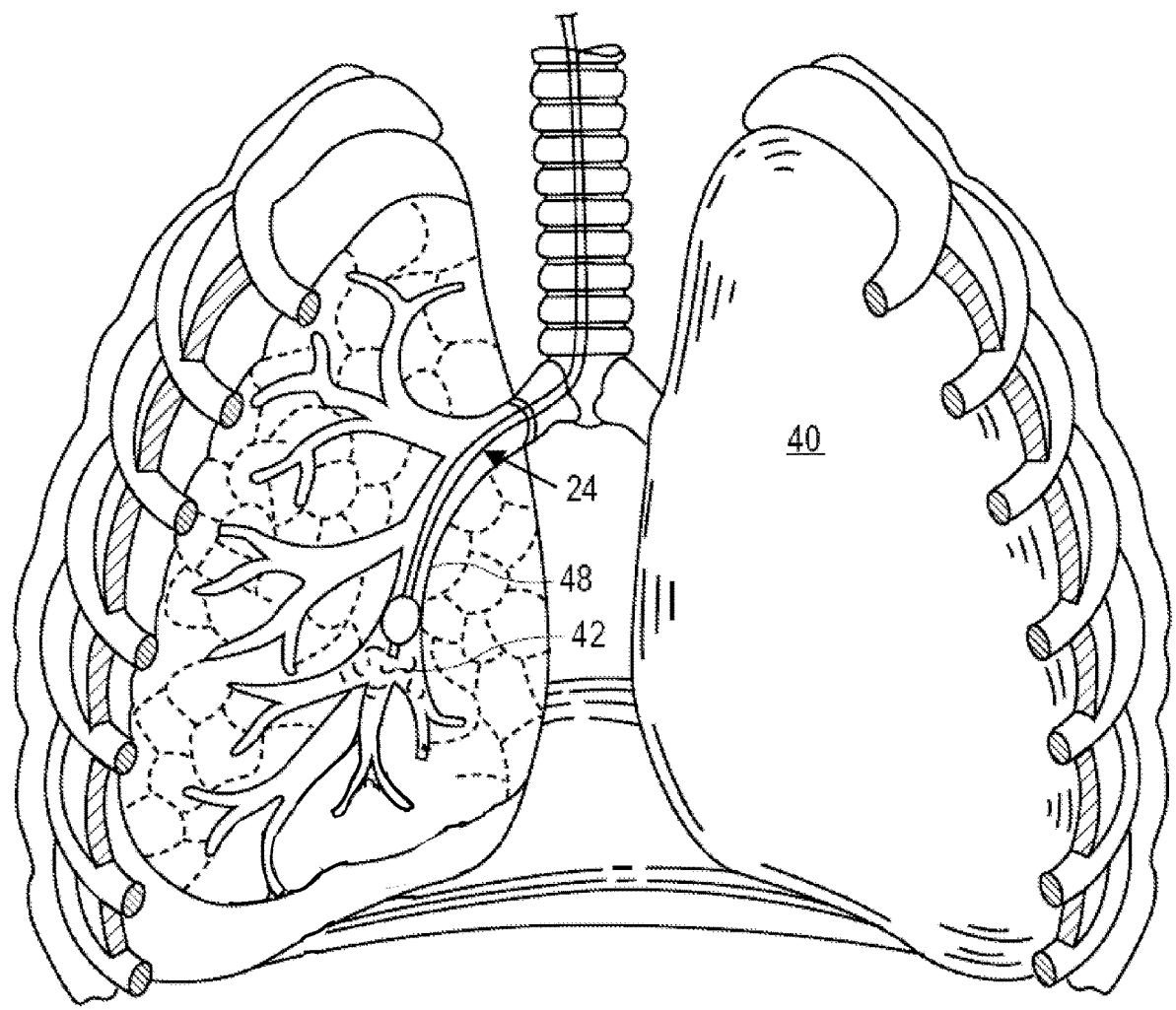
FIG. 3 illustrates the system of FIGS. 1-2 delivering vapor to the lungs of a patient.

FIG. 3 illustrates one method of treating a patient's lung 40 embodying features of the invention that includes delivering a heated condensable vapor 42 to the airways 48 of lung tissue, so as to create necrosis of the tissue of the nodule, the tissue of terminal bronchioles, and parenchymal tissue. In one embodiment, the catheter-based system of FIGS. 1-2 can be used to access the lung tissue, either with or without the aid of a bronchoscope. The distal tip of the catheter can be placed in proximity to the target lung tissue. Vapor generated by generator 12 can be delivered through the catheter to ablate the targeted tissue of the lung nodule.

A method of determining a treatment plan for LVR will now be described. In some embodiments, the treatment can include delivery of vapor to ablate the lung tissue once the treatment plan has been determined. First, a Tissue-to-air ratio (TAR) of each lung segment of the lungs can be calculated by dividing the tissue mass of a segment by the air volume of that segment. The TAR can be calculated, for example, by a processor or electronic controller of the system described above, based segmental tissue and air volumes derived from imaging or a diagnostic evaluation of the lungs. Alternatively, a physician or medical provider can calculate the TAR of each lung segment. The TAR of each lung segment can be used to quantitatively characterize a disease state of the lung tissue. The TAR of each lung segment can be used to calculate a heterogeneity index (HI) of the segments, which is the ratio of the TAR of the ipsilateral lobe to the TAR of the segment. A further diagnostic evaluation of the patient's lungs can determine additional parameters of the patient's lung, including the mass of each lung segment and the volume of each lung segment.

After the TAR of each lung segment has been calculated, the electronic controller of the system, or a physician, can compile a list of potential treatments that include a first treatment that targets a first segment of a first lobe of the first lung, and a second treatment that targets a second segment of a second lobe of the second lung. Since this list of potential treatments can include several potential treatment plans (dozens or more), a logic workflow can be used to determine the optimal segment selection for treatment. This disclosure describes various methodologies that can be used to exclude treatment plans from the list of potential treatment plans to identify the safest and most effective treatment plan for LVR therapy.

In one exemplary treatment plan, one lobe in a patient lung is treated (e.g., with condensable vapor to ablate the lung tissue). For example, in one embodiment vapor can be delivered in a first treatment to one segment, preferably the most diseased segment, of an upper lobe of a patient's lung. After treatment of the first lobe, the treatment plan typically requires a period of time for healing and reaction from this treatment to occur (typically 3 months). Next, vapor can be delivered in a second treatment to one or two segments of a lobe in the opposite lung. Generally, the first treatment targets 50%+/−20% (absolute) volume reduction of the first lobe, and the second treatment targets 60%+/−20% (absolute) volume reduction of this second (and possibly third) lobes. Although the preferred treatment of lung tissue includes delivering condensable vapor to the tissue to ablate the lung tissue, other treatment methods, such as those described above in the background section, may be used in accordance with the treatment planning described herein. The overall volume reduction target sum of the lung volume reduction percentages between the first and second treatments can be approximately 110%+20%/−15% (absolute). This treatment plan considers the TAR of the lobes to be treated as a first priority; however, the further the most diseased segment is from the targeted volume reduction, the greater chance that another lobe would be selected. The treatment plans described herein typically provide for treatment of the superior (upper) lobes of the lungs. However, a similar methodology can be applied to treat the inferior (lower) lobes of the lungs in other embodiments.

According to the treatment plan described in the paragraph above, the following rules can be used for selecting the optimal segment(s) to treat during the first and second treatments. These rules can be applied to select the optimal segments and lobes to treat for each particular patient so as to maximize the effectiveness of the vapor therapy for that patient.

The human body comprises two lungs, and a total of five lobes. The right lung has three lobes, including the superior (upper), middle, and inferior (lower) lobes, and the left lung has two lobes, the superior and inferior lobes. Each lobe of the lungs includes several lung segments. As described above, patients with severe emphysema typically have lung segments within a lobe that are significantly more diseased than other segments within that lobe. Since not all segments in each lobe are typically diseased, a treatment plan needs to be devised so as to not treat healthy lung segments.

Figure 4A:
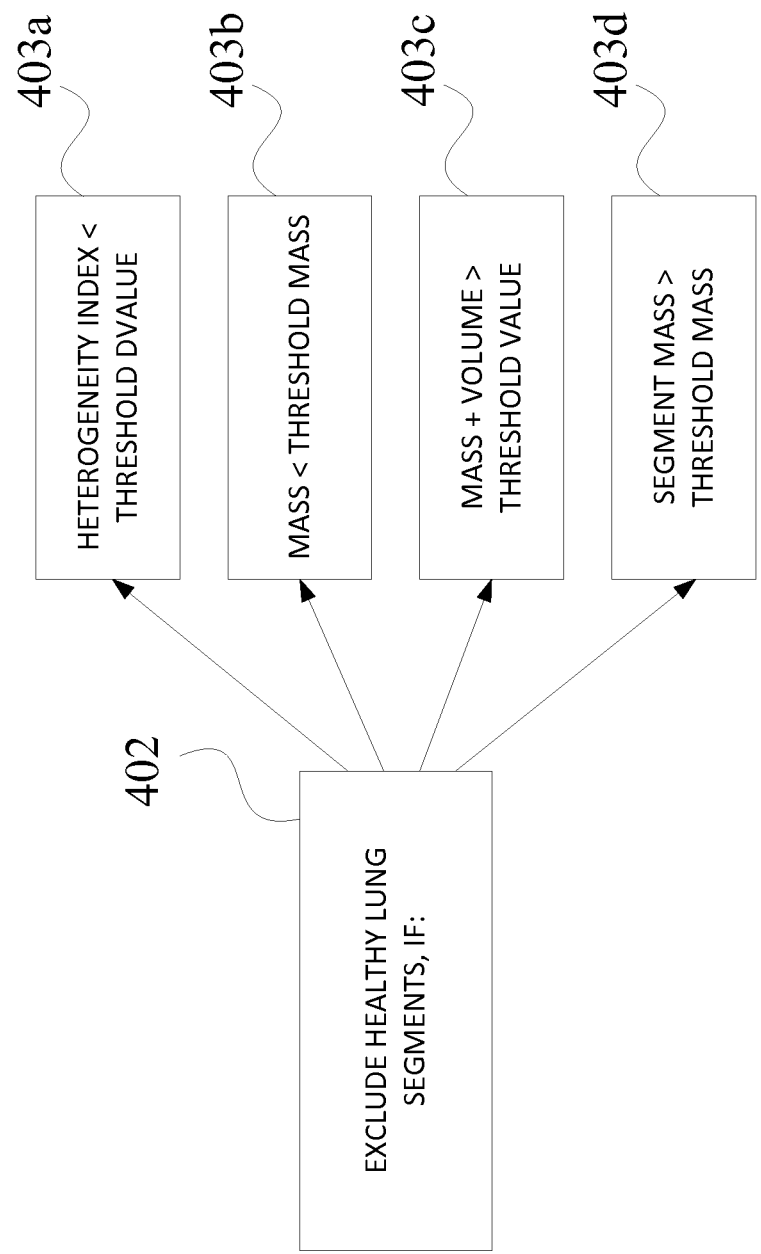
FIGS. 4A-4B illustrate segment exclusion rules for treatment planning.
Figure 4B:
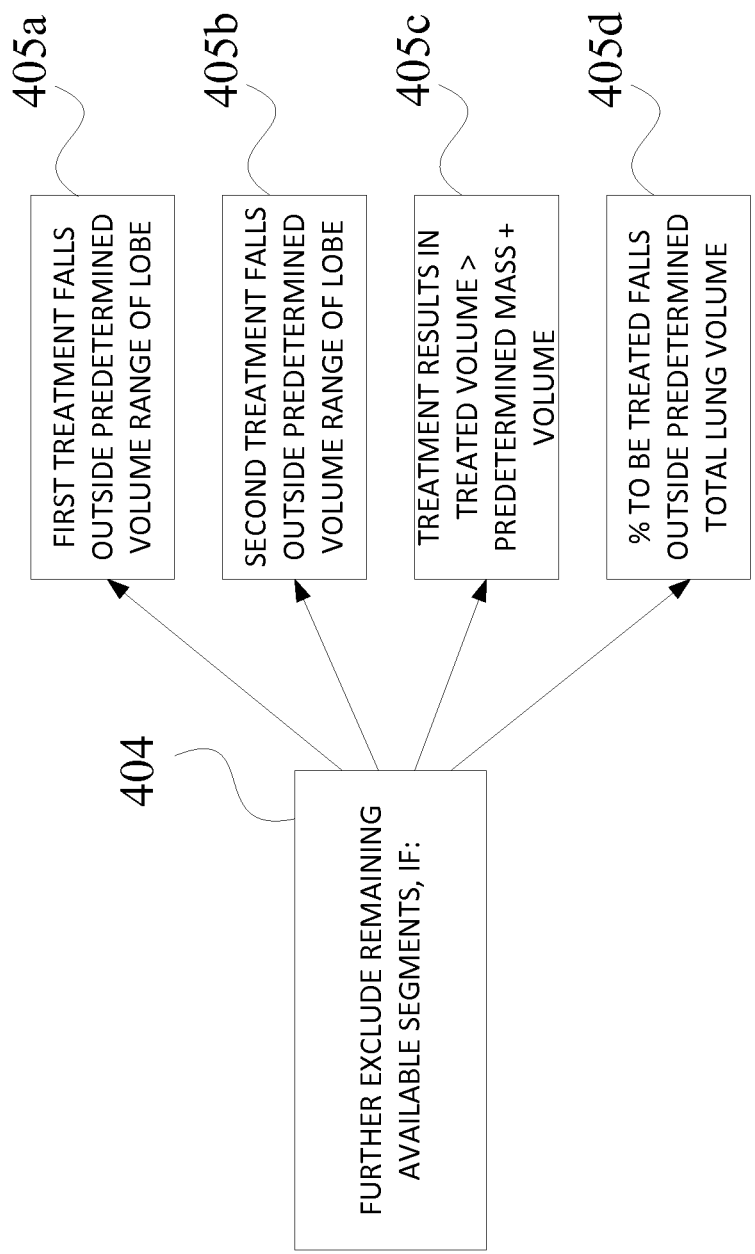

The flowchart of FIGS. 4A-4B describes the methodology taken to exclude healthy lung segments from treatment, according to one embodiment of a method of treating a lung with vapor. All method steps described in FIGS. 4A-4B can be performed or carried out by a processor or electronic controller of the system described above. The data with which the processor can determine which segments to exclude can be based on a diagnostic evaluation of the patient's lungs, e.g., diagnostic imaging of the lungs. Alternatively, the method can be carried out by a physician or medical provider.

Step 402 of the flowchart of FIG. 4A aims to exclude individual healthy lung segments from treatment. Referring to step 403a of FIG. 4A, lung segments can be excluded from the list of potential treatment plans if they have a heterogeneity index less than a threshold heterogeneity value. In one embodiment, lung segments can be excluded if the HI is less than 1.2. As defined above, the HI considers the tissue-to-air ratio of the particular segment in relation to the average of all the segments in the same lobe. According to one embodiment, a HI less than 1.2 is an indication that the segment being evaluated is "healthy" based on TAR. The controller or processor of the system can evaluate the HI of each lung segment and exclude the segment from treatment if the HI is less than the threshold heterogeneity value (e.g., less than 1.2). Alternatively, this evaluation can be made by a physician.

In step 403b of FIG. 4A, lung segments can be excluded from treatment if they have a mass less than a minimum threshold mass. In one embodiment, segments can be excluded if they have a mass less than 13 g. The mass of the segment being considered can be determined based on imaging of the lung, either by the controller of the system or by a physician, and the controller or the physician can made the determination to exclude the segment based on the mass of the segment. Lung segments with a mass of less than 13 g can be excluded from treatment because segments this small typically require such a short treatment time (less than 3 seconds).

Referring to step 403c of FIG. 4A, segments can also be excluded by either the controller of the system or a physician if the tissue volume (computed from its mass, assuming 1 gram of tissue mass=1 ml of tissue volume) plus the air volume of the segment being evaluated is greater than a threshold value. In one embodiment, the segment can be excluded if the tissue mass in grams (assuming 1 g of tissue=1 ml of tissue volume) plus air volume in ml is greater than 1700.

Finally, referring to step 403d of FIG. 4A, a segment can be excluded by a controller of the system or a provider if the segment mass is greater than a maximum threshold mass. In one embodiment, the segment can be excluded from treatment if the mass is greater than 48 g. Segments with masses greater than the maximum threshold mass can be excluded from treatment since they require treatment times longer than is desirable for the patient (e.g., treatment times greater than 10 sec).

Step 404 of FIG. 4B provides methodology for evaluating the feasibility of a treatment plan as a whole (first and second treatments) in view of the individual segment exclusions from step 402. As described above, a first treatment typically treats a first segment in a first lobe of a first lung, and the second treatment can treat a second segment (and sometimes a third segment) in a second lobe of the second lung. For example, a first treatment can comprise delivering vapor to one segment in the upper lobe of the left lung, and a second treatment can comprise delivering vapor to two segments in the upper lobe of the right lung. At step 404 of FIG. 4, a controller or provider can evaluate all possible treatment plans (first and second treatments) after individual segments have been excluded (from step 402) and can further exclude the remaining available segments according to the following rules.

In step 405A of FIG. 4B, if a segment to be treated in the first treatment makes up a volume that falls outside of a predetermined volume range of the entire lobe, then that segment can be excluded from the list of possible treatment plans. In one embodiment, if the first treatment would require treating a segment that falls outside of 30-70% of the total volume of the lobe (e.g., the segment is less than 30% of the volume of the lobe or greater than 70% of the volume of the lobe) the segment can be excluded from the list of possible treatment plans. For example, if a segment in a potential first treatment makes up 25% of the lobe, then the segment falls outside of the range of 30-70% and can be excluded.

Similarly, referring to step 405b, if a segment to be treated in the second treatment makes up a volume that falls outside of a predetermined volume range of the entire lobe, then the segment can be excluded from the list of possible treatment plans. In one embodiment, if the second treatment would require treating a segment that falls outside of 40-80% of the total volume of the lobe (e.g., the segment is less than 40% of the volume of the lobe or greater than 80% of the volume of the lobe) the segment can be excluded from the list of possible treatment plans. For example, if a segment in a potential second treatment makes up 85% of the lobe, then the segment falls outside of the range of 40-80% and can be excluded.

In step 405c, if the first or second treatment would result in a total treated mass (in grams) plus volume (in ml) greater than a threshold mass plus volume (such as 1700), then it can be excluded.

In step 405*d*, treatment options can be excluded if the combined percentage of the segments to be treated with respect to the total volume of both lobes falls outside a predetermined range of the total volume of both lungs. The percentage range can be taken on a scale of 200% (e.g., 100% for the first lung plus 100% of the second lung) for the combined first and second treatments. If a segment to be treated in the first treatment plus a segment to be treated in the second treatment falls outside of the predetermined range, then the options of segments being evaluated can be excluded. In one embodiment, if the first and second treatments would result in treatment of the lungs falling outside a range of 95%-130%, then the segment options can be excluded.

For example, if first treatment would result in treatment of 30% of the first lobe, and the second treatment would result in treatment of 40% of the second lobe, the combination of the first and second treatments would treat only 70% (out of 200%) of the two lobes/lungs. This combined treatment volume of 70% falls outside of the preferred volume range of 95-135% in step 405D.

Steps 402 and 404 above eliminate all segments (or combinations of segments) for the list of possible treatment plans. After all possible treatment plans have been determined, the available treatment plans can be ranked according to the rules described in FIG. 5. Once again, these determinations undertaken in the flowchart of FIG. 5 can be performed by a processor or electronic controller of the vapor system described above. Alternatively, they can be determined by a physician or medical provider.

Figure 5:
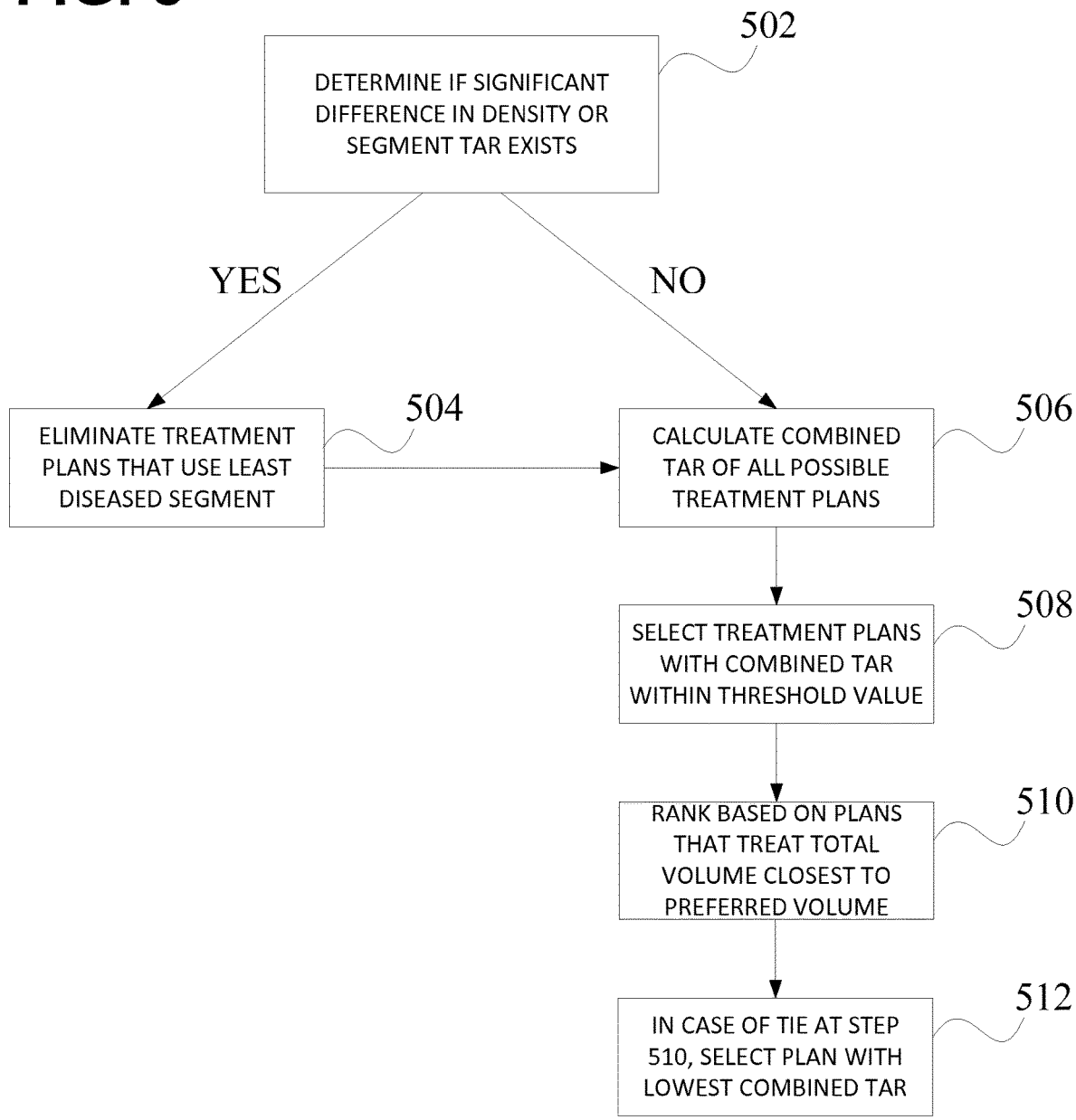
FIG. 5 illustrates treatment plan ranking rules for treatment planning.

First, referring to step 502 of FIG. 5, the electronic controller or medical provider can determine if a significant difference in density or segment TAR in the available segments of each lobe exists. This determination aims to find the balance between treating the most diseased segment in the lobes and treating the appropriate volume of the lobes. In one embodiment, a significant difference in density or segment TAR can be defined as greater than 2% difference between the segments in each lobe. As described above, the TAR of the various lung segments can be used to quantify a disease state of the lung tissue. In the present example, a difference of 2% absolute difference is used as significant quantifier of a diseased state in the lung tissue, but any difference could be used as significant depending on the treatment modality, patient type, and understanding of the disease.

If at step 502, it is determined that there exists a significant difference in segment TAR between the available segments, then at step 504 the controller or medical provider can conditionally eliminate any available treatment plans from the list of potential treatment plans that use the "least diseased" (e.g., highest TAR) segment in that lobe.

For an example of steps 502 and 504, if a first segment RB1 has a TAR of 7%, a second segment RB2 has a TAR of 10%, and a third segment RB3 has a TAR of 8%, by this definition, there is a significant difference in segment TAR between the segments because there exists a 3% difference between any two of the three segments within the lobe (here, the 3% difference exists between RB1 and RB2). Applying step 504 to this example, least diseased segment (the second segment RB2 with a TAR of 10%) can be conditionally eliminated from the list of available treatment plans. Thus, the controller or medical provider will determine not to treat the least diseased segment, but will still consider treating the remaining segments (in this example, the remaining segments have TARs of 7% and 8%).

Advancing from step 504 of FIG. 5 (or directly from step 502 if there is an insignificant difference in segment TAR) arrives at step 506 of FIG. 5. At step 506, the controller or provider can calculate a combined TAR of all possible treatment plans from the remaining options, determine the lowest combined TAR value, and can select all treatment plans having a combined TAR within a specified range of the lowest combined TAR value. A combined TAR is defined as the mass of all segments in each treatment option, divided by the volume of all segments in that treatment option. In some embodiments, the combined TAR can be an average of the segments, or alternatively it can be weighted based on the volume and/or mass of segments. A combined TAR will typically evaluate 1 segment from the first lobe to be treated (during the first treatment), and then will evaluate 1-2 segments from the second lobe to be treated (during the second treatment). The combined TAR for the first and second treatments can then be determined.

In one embodiment, as shown in step 508 of FIG. 5, all treatment plan options having a combined TAR within a threshold range of the lowest combined TAR can be selected. In one embodiment, the threshold range can be 0.3%.

If multiple treatment plan options satisfy the criteria of step 508, then the remaining options can be ranked at step 510 of FIG. 5 based on treatment plans that would result in treating a total volume of the lung closest to a preferred volume are selected as the primary option. In one embodiment, the ideal total volume to be treated between both lungs is 110% of a lobe (out of 200% for two lobes combined).

At step 512 of FIG. 5, if multiple treatment plans have a combined TAR within the threshold range of the lowest combined TAR, and also would treat a total volume at or near the ideal total volume to be treated, then the treatment plan with the lowest combined TAR is preferred.

If the method described above does not result in three available treatment plans, then the controller or provider can select the next lowest combined TAR, and repeat the steps above to arrive at 3 treatment planning options.

By way of example to understand steps 506-512, in one example at step 506 a patient has potential treatment plans with a combined TAR of 8%, 9%, and 10%, respectively. In this example, the lowest combined TAR averages to 9%. Next, the controller or the provider can, at step 508, look for any other treatment plans falling within the threshold range (e.g., 0.3%) of this lowest combined TAR. Thus, treatment plans for this patient with a combined TAR average of 8.8%, and of 9.3%, would fall within the threshold range. Once the available treatment plans within the threshold range of the lowest combined TAR are identified, preference is given, at step 510, to the treatment plan that is closest to the ideal total volume to be treated (e.g., closest to 110%). The best treatment plan available is a treatment plan that falls within the threshold range of the lowest combined TAR, that is closest to the ideal total volume to be treated. Given the example of this paragraph, if the treatment plan having a combined TAR average of 9% would treat 105% of the two lobes, but a different treatment plan having a combined TAR average of 9.3% would treat 110% of the two lobes, then the latter treatment plan is preferred. The intent of this methodology is to rank treatment options closest to the ideal total volume to be treated (thought at the time of this writing to be approximately 110%).

The methods described above refer to segments of the lung. However, it should be understood that the methods can also be applied to subsegments of the lungs as well.

FIGS. 6A-6D will walk through one example of determining a treatment plan according to the principles laid out above. FIG. 6A shows all the different combinations of segments to be treated in the upper lobes of a patient. In this example, the left upper lobe (LUL) can include segments LB1, LB2, LB3, and LB1+2, and the right upper lobe (RUL) can include segments RB1, RB2, and RB3. Referring still to FIG. 6A, Method 1 (treatment plan option 1) would provide a first treatment to segment RB1 of the right upper lobe, followed by a second treatment to segments LB1 and LB2 of the left upper lobe. The segment treated in the first treatment is indicated by the number "1" in the chart, and the segment(s) treated in the second treatment are indicated by the "2" (and where applicable, "3"). Method 2 (treatment plan option 2) would provide a first treatment to RB1 and a second treatment to LB1 and LB3. The various permutations of possible treatments are shown in the remaining Methods 3-33 of FIG. 6A.

FIG. 6B illustrates the various parameters of each segment that will be used for treatment planning, including the TAR of each segment, the HI of each segment, the air volume of each segment, the mass of each segment, the total volume of each segment, the percentage of the lobe that each segment comprises, and the LL TAR, or lower lobe TAR of each lung.

FIG. 6C applies the exclusionary rules outlined above in FIG. 4 to the individual segments in each possible treatment plan. For example, in FIG. 6C, Methods 5-8, 16-18, 27-30 and 33 can be excluded from the list of treatment plans because the first treatment (Tx. 1) of delivering vapor to RB2, with a percentage of the lobe of 24%, falls below the range of 30-70% defined in step 404 of FIG. 4 above. (In an output or display, these and other excluded blocks can be marked with red text and/or shading to show an exclusion.) Similarly, Methods 13-15 can be excluded since the first treatment of delivering vapor to LB1+2 would fall above the range of 30-70%. As seen in FIG. 6C, Methods 28-33 can also be excluded since they require the second treatment (Tx. 2) to deliver vapor to lobes falling below the range of 40-80% defined above. The remainder of columns in FIG. 6C show each of the exclusions defined above, including eliminating treatment plans that treat less than 95% or greater than 130% of the two lobes, or have a segmental HI and mass greater than 48 g. The Methods lacking any exclusions are Methods 1-3, 9, 19, 20, 22 and 23. These Methods may be marked with green shading in an output or display.

FIG. 6D identifies the least diseased segments in which there is a significant difference in TAR between the available segments. As described above in FIG. 5, these segments can be excluded from treatment. The data in FIGS. 6A-6D results in only a single method, Method 1, that does not conditionally eliminate any "least diseased" segments and satisfies the other requirements of FIGS. 4 and 5. Method 1 therefore becomes the preferred, or best treatment plan. As described above, 3 total options are desired, so the controller or provider can return to the list, select the next lowest "combined TAR" and repeat the steps described above including any previously conditionally eliminated options. Going through this process for the data of FIGS. 6A-6D results in the selection of Method 2 as the 2nd best option and Method 22 as the 3rd best option.

There may be patients for whom the treatment planning methodology outlined above concludes that no treatment is possible, i.e., all potential treatment plans are excluded. For such patients, revisiting one or more of the exclusion criteria on a subsegmental basis may result in an acceptable treatment plan. For example, a lung segment treatment plan that was excluded on the basis of the segment's tissue mass in grams plus air volume in milliliters is greater than 1700 may be recalculated for a subsegment of that lung segment. If the subsegment qualifies, then that subsegment can be treated.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A treatment planning system for assisting a physician perform bronchoscopic lung volume reduction, the system including a processor operable to perform the following:
    compile a plurality of potential lung volume combinations for lung volume reduction in first and second lungs of a patient based on diagnostic information derived from images relating to the patient's first and second lungs, wherein each potential lung volume combination includes at least one lung volume from the first lung and at least one lung volume from the second lung; and wherein each of the lung volumes is a lung segment or lung subsegment;
    compute a plurality of diagnostic values for each lung volume of said potential lung volume combinations;
    determine a segment exclusion rule operable to exclude one or more of the potential lung volume combinations based on comparing the diagnostic value from the computing step to a threshold value or range;
    exclude at least one of the potential lung volume combinations based on said segment exclusion rule; and
    identify at least one preferred lung volume combination not excluded from the potential lung volume combinations for the bronchoscopic lung volume reduction, wherein the preferred lung volume combination targets diseased lung volumes while also targeting a preferred combined volume of the first and second lungs based on the computed diagnostic values to assist the physician to perform the bronchoscopic lung volume reduction.

2. The system of claim 1 wherein the diagnostic values are selected from the group consisting of a tissue-to-air ratio, a heterogeneity index, an air volume, a mass, and a percentage of a lobe of each volume of the first and second lungs.

3. The system of claim 1 wherein compiling comprises compiling a list of potential treatments that include a first treatment that targets a first segment of a first lobe of the first lung, and a second treatment that targets a second segment of a second lobe of the second lung.

4. The system of claim 3 wherein the second treatment also targets a third segment of the second lobe of the second lung.

5. The system of claim 1 wherein the segment exclusion rule requires that lung volume combinations including lung segments that have a heterogeneity index under 1.2 be excluded.

6. The system of claim 1 wherein the segment exclusion rule requires that lung volume combinations including lung segments that have a mass less than 13 grams be excluded.

7. The system of claim 1 wherein the segment exclusion rule requires that lung volume combinations including segments having a tissue mass in grams plus air volume milliliters greater than 1700 be excluded.

8. The system of claim 1 wherein the segment exclusion rule requires that lung volume combinations that have a mass greater than 48 grams be excluded.

9. The system of claim 1 wherein the segment exclusion rule requires that lung volume combinations including treatment of the first lung that treats less than 30% of the volume of the first lung or more than 70% of the volume of the first lung be excluded.

10. The system of claim 1 wherein the segment exclusion rule requires that lung volume combinations including treatment of the second lung that treats less than 40% of the volume of the second lobe or more than 80% of the volume of the second lobe be excluded.

11. The system of claim 1 wherein the segment exclusion rule requires that lung volume combinations including a treatment of the first and second lungs resulting in less than 95% or greater than 130% of a combined percentage of volume of the first and second lungs be excluded.

12. The system of claim 1 wherein the plurality of potential lung volume combinations includes at least one lung segment from the first lung and at least one lung segment from the second lung.

13. The system of claim 12 wherein the at least one preferred lung volume combination requires treatment of segments with an insignificant difference in tissue-to-air ratios (TARs).

14. The system of claim 13 wherein the insignificant difference comprises a difference of less than 2% between the TARs of the lung segments of the lung volume combination.

15. The system of claim 13 wherein the at least one preferred volume combination requires treatment of lung segments that rank closest to 110% of a combined percentage of the first and second lungs to be treated.

16. The system of claim 12, wherein the at least one preferred volume combination comprises treatment by applying lung volume reduction therapy to at least one lung segment in the first lung and at least one lung segment in the second lung.

17. The system of claim 16, further comprising a vapor ablation catheter, and wherein the lung volume reduction therapy comprises delivering condensable vapor to the patient's lungs.

18. The system of claim 1 wherein the compiling comprises compiling a list of potential volume combinations in a ranked order.

19. The system of claim 18 further comprising a display for displaying the list.

20. The system of claim 19 wherein each lung volume is a lung segment.

* * * * *